United States Patent
Fang et al.

(10) Patent No.: US 11,574,220 B2
(45) Date of Patent: Feb. 7, 2023

(54) METHOD AND DEVICE FOR EVALUATING COOKING QUALITY

(71) Applicant: FOSHAN SHUNDE MIDEA ELECTRICAL HEATING APPLIANCES MANUFACTURING CO., LIMITED, Foshan (CN)

(72) Inventors: Zhen Fang, Foshan (CN); Ying Su, Foshan (CN); Jing Li, Foshan (CN); Xinyuan Wang, Foshan (CN); Shanshan Cao, Foshan (CN); Liying Wang, Foshan (CN)

(73) Assignee: FOSHAN SHUNDE MIDEA ELECTRICAL HEATING APPLIANCES MANUFACTURING CO., LTD., Foshan (CN)

( * ) Notice: Subject to any disclaimer, the term of this patent is extended or adjusted under 35 U.S.C. 154(b) by 1264 days.

(21) Appl. No.: 15/963,938

(22) Filed: Apr. 26, 2018

(65) Prior Publication Data

US 2018/0247212 A1    Aug. 30, 2018

Related U.S. Application Data

(63) Continuation of application No. PCT/CN2016/111535, filed on Dec. 22, 2016.

(30) Foreign Application Priority Data

Sep. 14, 2016    (CN) .......................... 201610826083.9

(51) Int. Cl.
*G06N 5/04*    (2006.01)
*G06Q 30/02*    (2012.01)
(Continued)

(52) U.S. Cl.
CPC .............. *G06N 5/046* (2013.01); *A47J 36/00* (2013.01); *G06Q 30/0201* (2013.01);
(Continued)

(58) Field of Classification Search
CPC ......... A47J 36/00; G01N 33/10; G06N 5/046; G06Q 30/0201; G06Q 30/0278; G06Q 30/0282; G16Y 10/80; G16Y 40/20
See application file for complete search history.

(56) References Cited

U.S. PATENT DOCUMENTS

2005/0129818 A1\* 6/2005 Yamamoto .............. A23L 7/126
426/502
2009/0274815 A1\* 11/2009 Kobayashi ............ A23L 29/212
426/578
(Continued)

FOREIGN PATENT DOCUMENTS

CN    101825556 A    9/2010
CN    102156129 A    8/2011
(Continued)

OTHER PUBLICATIONS

Foshan Shunde Midea Electrical Heating Appliances Manufacturing Co., Ltd., The Third Office Action, CN Application No. 201611036149.0, dated Aug. 9, 2021, 18 pgs.
(Continued)

*Primary Examiner* — Thien M Le
(74) *Attorney, Agent, or Firm* — Morgan, Lewis & Bockius LLP (57) ABSTRACT

Disclosed is a method for evaluating cooking quality that includes: in response to receiving evaluation information of a food sent by a terminal, retrieving an assessment result corresponding to the food, the assessment result being an assessment result of the cooking quality of a cooking appliance; and determining an evaluation result of the cook-
(Continued)

| Dimensions | Assessment Indexes | Weights | Superior Level 1000 | First Level 800 | Second Level 600 | Third Level 400 | Disqualified |
|---|---|---|---|---|---|---|---|
| Appearance | Surface Flatness | 11% | ≤10mm | 10-15mm | 15-20mm | 20-30mm | ≥30mm |
| | Loftiness | 11% | ≥170% | 165-170% | 160-165% | ≤160% | Null |
| | Expansion Rate | 11% | 160% | 155-160% | 150-155% | ≤150% | Null |
| Palatability | Average Water Content | 24% | 62%±0.1% | 61-63% | 60-61%, 63-64% | 58-60%, 64-66% | ≤58%, ≥66% |
| | Textural Hardness | 15% | 2050g±10g | 2000-2100g | 1900-2000g, 2100-2200g | ≤1900g, ≥2200g | Null |
| | Gelatinization Degree | 28% | ≥96% | 93-96% | 90-93% | 80-90% | ≤80% |
| Description | Each index includes five levels respectively corresponding to different assessment scores. Each assessment index has its own weight, and the total assessment score equals ∑(each assessment score times its weight) | | | | | | |
| Conclusion | The maximum score is 1000 points. Grade A ("Excellent"): 900-1000 points; Grade B ("Good"): 800-900 points; Grade C ("Qualified"):600-800 points; Grade D ("Poor"): below 600 points or there is at least one disqualification | | | | | | | ing quality of the cooking appliance based on the assessment result, the evaluation information, and a preset evaluation rule. Also disclosed is a device for evaluating cooking quality. With this disclosure, both the assessment result and the evaluation information are weighted in computing the evaluation result of the cooking quality of the cooking appliance. Such an evaluation result not only reflects users' subjective evaluation of the cooking quality, but it also reflects an objective and tenable evaluation of the cooking quality, making the evaluation of the cooking quality more reasonable.

18 Claims, 4 Drawing Sheets

(51) Int. Cl.
  *G16Y 10/80* (2020.01)
  *G16Y 40/20* (2020.01)
  *A47J 36/00* (2006.01)
  *G01N 33/10* (2006.01)

(52) U.S. Cl.
  CPC ..... *G06Q 30/0278* (2013.01); *G06Q 30/0282* (2013.01); *G16Y 10/80* (2020.01); *G16Y 40/20* (2020.01); *G01N 33/10* (2013.01)

(56) References Cited

U.S. PATENT DOCUMENTS

| | | | | |
|---|---|---|---|---|
| 2011/0262613 | A1* | 10/2011 | Cho | A23L 23/00 426/589 |
| 2012/0019674 | A1* | 1/2012 | Ohnishi | G08C 17/00 348/207.1 |
| 2012/0045562 | A1* | 2/2012 | Watanabe | A23L 29/219 426/578 |
| 2012/0207880 | A1* | 8/2012 | Shin | A21D 13/064 426/558 |
| 2018/0303142 | A1* | 10/2018 | Hagiwara | A23L 27/88 |

FOREIGN PATENT DOCUMENTS

| | | |
|---|---|---|
| CN | 202069423 U | 12/2011 |
| CN | 102507882 A | 6/2012 |
| CN | 104238390 A | 12/2014 |
| CN | 105078200 A | 11/2015 |
| CN | 105212685 A | 1/2016 |
| CN | 105425643 | 3/2016 |
| CN | 105512789 A | 4/2016 |
| EP | 1137323 A2 | 9/2001 |
| JP | 2008-146196 A | 6/2008 |
| JP | 2008-146196 A | 6/2009 |
| JP | 2009139110 A | 6/2009 |
| JP | 2014-176396 A | 9/2014 |
| KR | 20040108040 A | 12/2004 |
| KR | 1020110055215 A | 5/2011 |
| KR | 1020120121382 A | 11/2012 |

OTHER PUBLICATIONS

Kim et al., "Comparison of Cooking Properties Between the Functionally Fortified and Regular Rices Using Electric and Pressure Cookers," Department of Food Science and Nutricion, Yongin University, Apr. 12, 2004, Korean J. Food Culture, vol. 19, No. 3 (2004), pp. 359-368, 10 pgs.
Foshan Shunde Midea Electrical Heating Appliances Manufacturing Co. Ltd., Extended European Search Report, EP16908361.5, dated Jul. 4, 2018, 6 pgs.
Office Action, CN201611036149.0, dated Feb. 3, 2020, 6 pgs.
Notice of Reasons for Refusal, JP2017-559691, dated Nov. 26, 2018, 4 pgs.
Notification of Reasons for Refusal, KR10-2017-7032239, dated Oct. 31, 2018, 5 pgs.
Notice of Final Rejection, KR10-2017-7032239, dated May 29, 2019, 9 pgs.
Midea, International Search Report and Written Opinion, PCT/CN2016/111535, dated May 31, 2017, 14 pgs.
Tao, Min et al., "Application research of food sensory evaluation in cooking performance test of household electrical appliances," China Appliance Technology, application, Jun. 1, 2014, 3 pgs.
Midea Group Co., Ltd., Notification to Grant Patent Right for Invention, CN Patent Application No. 201611036149.0, dated Sep. 8, 2022, 6 pgs.
Midea Group Co., Ltd., IPRP, PCT/CN2016/111535, dated Mar. 19, 2019, 4 pgs.

* cited by examiner

| Dimensions | Loftiness (%) | Flatness (mm) | Average Water Content (%) | Hardness (g) | Expansion Rate (%) | Gelatinization Degree (%) |
|---|---|---|---|---|---|---|
| Optimal Trend Values | 170% | The less the better | 62% | 2050 | 160% | 100% |

FIG. 5

| Dimensions | Assessment Indexes | Weights | Superior Level | First Level | Second Level | Third Level | Disqualified |
|---|---|---|---|---|---|---|---|
|  |  |  | 1000 | 800 | 600 | 400 |  |
| Appearance | Surface Flatness | 11% | ≤10mm | 10-15mm | 15-20mm | 20-30mm | ≥30mm |
|  | Loftiness | 11% | ≥170% | 165-170% | 160-165% | ≤160% | Null |
|  | Expansion Rate | 11% | 160% | 155-160% | 150-155% | ≤150% | Null |
| Palatability | Average Water Content | 24% | 62%±0.1% | 61-63% | 60-61%, 63-64% | 58-60%, 64-66% | ≤58%, ≥66% |
|  | Textural Hardness | 15% | 2050g±10g | 2000-2100g | 1900-2000g, 2100-2200g | ≤1900g, ≥2200g | Null |
|  | Gelatinization Degree | 28% | ≥96% | 93-96% | 90-93% | 80-90% | ≤80% |
| Description | | | Each index includes five levels respectively corresponding to different assessment scores. Each assessment index has its own weight, and the total assessment score equals ∑(each assessment score times its weight) | | | | |
| Conclusion | | | The maximum score is 1000 points. Grade A ("Excellent"): 900-1000 points; Grade B ("Good"): 800-900 points; Grade C ("Qualified"):600-800 points; Grade D ("Poor"): below 600 points or there is at least one disqualification | | | | |

METHOD AND DEVICE FOR EVALUATING COOKING QUALITY

PRIORITY CLAIM AND RELATED APPLICATION

This application is a continuation application of PCT/CN2016/111535, entitled "METHOD AND DEVICE FOR EVALUATING COOKING QUALITY" filed on Dec. 22, 2016, which claims priority to Chinese Patent Application No. 201610826083.9, filed with the State Intellectual Property Office of the People's Republic of China on Sep. 14, 2016, both of which are incorporated herein by reference in their entirety.

TECHNICAL FIELD

This disclosure relates generally to the technical field of quality assessment and evaluation, and more particularly relates to a method and device for evaluating cooking quality.

BACKGROUND

In purchasing cooking appliances such as rice cookers, consumers would often desire to know whether the cooking quality of various cooking appliances is capable of meeting their needs. But currently the evaluation of the cooking quality, e.g., evaluation on the appearance and taste of a food cooked by a cooking appliance, is generally obtained from the evaluations given by other product users. Such an evaluation method, however, is very subjective that people having different requirements with food taste may draw different evaluations towards the same product. Therefore, the evaluation result obtained with such an evaluation method cannot reflect an objective evaluation of the cooking quality of a cooking appliance.

SUMMARY

In view of the above, this disclosure provides a method and a device for evaluating cooking quality, which aim at addressing the technical problem of existing cooking quality evaluation methods failing to reflect an objective evaluation of the cooking quality.

In order to achieve the above end, this disclosure provides a method for evaluating cooking quality that includes: in response to receiving evaluation information of a food sent by a terminal, retrieving an assessment result corresponding to the food, the assessment result being an assessment result of the cooking quality of a cooking appliance; and determining an evaluation result of the cooking quality of the cooking appliance based on the assessment result, the evaluation information, and a preset evaluation rule.

In some embodiments, the cooking appliance is a rice cooker, and determining the evaluation result of the cooking quality of the cooking appliance may include: acquiring respective weights of the assessment result and the evaluation information; and computing the evaluation result based on the assessment result, the evaluation information, and their respective weights.

In some embodiments, the food is rice, and acquiring the respective weights of the assessment result and the evaluation information may include: acquiring a type of the rice; and acquiring the respective weights of the assessment result and the evaluation information according to the rice type.

In some embodiments, the cooking appliance is a rice cooker, and the method may further include, subsequent to determining the evaluation result of the cooking quality of the cooking appliance: retrieving identification information of the rice cooker; and storing in association the identification information, the assessment result, the evaluation information, and the evaluation result.

In some embodiments, the method may further include, subsequent to determining the evaluation result of the cooking quality of the cooking appliance: sending the evaluation result to the terminal so that the terminal can display the received evaluation result.

In some embodiments, the method may further include, prior to retrieving the assessment result of the cooking quality of the cooking appliance corresponding to the food: retrieving an assessment score of the cooking appliance on a preset assessment index, the assessment score being obtained by using a measuring device to measure the food cooked by the cooking appliance; and determining the assessment result of the cooking quality of the cooking appliance based on the acquired assessment score on the preset assessment index and a preset assessment rule.

In addition, in order to achieve the above object, this disclosure also provides a device for evaluating cooking quality that includes: a first acquisition module that retrieves an assessment result corresponding to a food in response to receiving evaluation information of the food sent by a terminal, the assessment result being an assessment result of the cooking quality of a cooking appliance; and an evaluation module that determines an evaluation result of the cooking quality of the cooking appliance based on the assessment result, the evaluation information, and a preset evaluation rule.

In some embodiments, the cooking appliance is a rice cooker, and the evaluation module may include: an acquisition unit configured for acquiring respective weights of the assessment result and the evaluation information; and a computation unit configured for computing the evaluation result based on the assessment result, the evaluation information, and their respective weights.

In some embodiments, the food is rice, and the acquisition unit may include: a first acquisition subunit configured for acquiring a type of the rice; and a second acquisition subunit configured for acquiring the respective weights of the assessment result and the evaluation information according to the rice type.

In some embodiments, the cooking appliance is a rice cooker, and the device may further include: a second acquisition module configured for acquiring identification information of the rice cooker; and a storage module configured for storing in association the identification information, the assessment result, the evaluation information, and the evaluation result.

In some embodiments, the device may further include: a transmission module configured for sending the evaluation result to the terminal so that the terminal can display the received evaluation result.

In some embodiments, the device may further include: a third acquisition module configured for retrieving an assessment score of the cooking appliance on a preset assessment index where the assessment score is obtained by using a measuring device to measure the food cooked by the cooking appliance; and an assessment module configured for determining the assessment result of the cooking quality of the cooking appliance based on the obtained assessment score on the preset assessment index and a preset assessment rule.

According to this disclosure, in response to receiving the evaluation information of a food sent by a terminal, the assessment result corresponding to the food is retrieved. Then an evaluation result of the cooking quality of the cooking appliance is determined based on the assessment result, the evaluation information, and a preset evaluation rule. Thus, both the assessment result and the evaluation information are weighted in obtaining the evaluation result of the cooking quality of the cooking appliance. Such an evaluation result not only reflects the users' subjective evaluation of the cooking quality, but it also reflects an objective and tenable evaluation of the cooking quality, making the evaluation of the cooking quality of the cooking appliance more reasonable.

Implementations, functional features and advantages of this disclosure will now be described in further detail with reference to the accompanying drawings.

DETAILED DESCRIPTION OF ILLUSTRATED EMBODIMENTS

It will be appreciated that various specific embodiments described herein are merely illustrative of the disclosure and are not intended to limit the disclosure.

Figure 1:
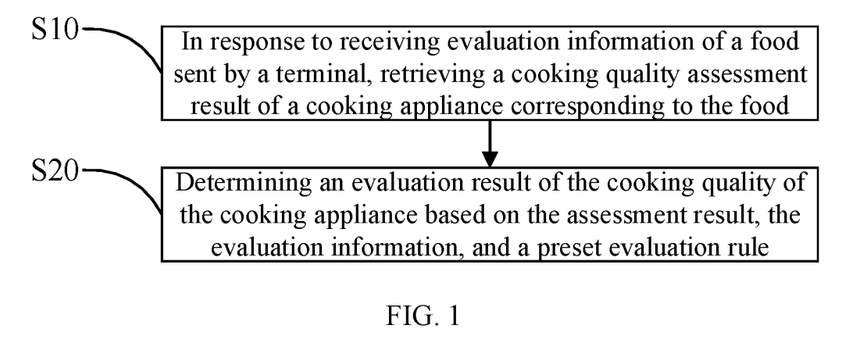
FIG. 1 is an illustrative flowchart of a first embodiment of a method for evaluating cooking quality in accordance with the disclosure.

A method for evaluating cooking quality is provided herein. FIG. 1 shows an illustrative flowchart of a first embodiment of the method for evaluating cooking quality in accordance with the disclosure.

In this embodiment, the method may include the following blocks which begin at block S10.

In block S10, in response to receiving evaluation information of a food sent by a terminal, an assessment result corresponding to the food is retrieved, where the assessment result is an assessment result of the cooking quality of a cooking appliance.

In this embodiment, an assessment system may be provided. An assessment result of the cooking quality of a cooking appliance can be input to the assessment system. The assessment system may store the identification information (e.g., a serial number) of a cooking device (e.g., a cooking appliance) and an assessment result of the cooking quality of the cooking device in association. The assessment system can be deployed in a server, a PC (personal computer), etc., and can be flexibly configured as needed. In some embodiments, the assessment system may include preset evaluation rules.

The following embodiment will be described by taking as an example a cooking appliance to be evaluated, a server, and rice cooked using the cooking appliance.

In this embodiment, in response to receiving evaluation information of a food sent from a terminal, the server may retrieve an assessment result of the cooking quality of the cooking appliance corresponding to the food. In particular, the server may first retrieve the identification information of the cooking appliance corresponding to the food, and then retrieve the assessment result of the cooking quality of the cooking appliance corresponding to the identification information from among the stored cooking quality assessment results; alternatively, the server may send an assessment result retrieval instruction containing the identification information to a device for evaluating the cooking quality of a cooking appliance, so that the device used for evaluating the cooking quality of a cooking appliance can return the cooking quality assessment result of the cooking appliance corresponding to the identification information.

It should be noted that users may score on a terminal such as a mobile phone on the aroma, color, taste, shape, hardness, etc., of the rice. For example, the user may input scores or grades on the terminal with regards to the aroma, color, taste, shape, hardness, etc. of the rice, and the terminal may then generate evaluation information based on the scores or grades input by the users, where the evaluation information may be an evaluation score or an evaluation grade. Users can also make an overall evaluation of the rice; that is, a user may enter only one evaluation score or evaluation grade. The method may then proceed to block S20.

In block S20, an evaluation result of the cooking quality of the cooking appliance is determined based on the assessment result, the evaluation information, and a preset evaluation rule.

In some embodiments, the assessment result is an assessment score of the cooking quality of the cooking appliance. The evaluation information is an evaluation grade which can be converted to an evaluation score according to grade ranking rules. For example, the evaluation grades may include three levels—"excellent," "good," and "poor". In the case where the maximum score is 100 points, for example, "excellent" would represent a score of 85 points and above, "good" would represent a score between 60 to 84 points, and "poor" would represent a score below 60 points. If the received evaluation grade is "excellent", then this evaluation grade can be converted to an evaluation score of 90 points or it can also be converted to a score of 95 points.

In this embodiment, the evaluation result of the cooking quality of the cooking appliance is determined based on the assessment result, the evaluation information, and the preset evaluation rule. In particular, the preset evaluation rule may include respective weights of the assessment result and the evaluation information so that the evaluation result can be computed based on the assessment result, the evaluation information, and their respective weights.

In one embodiment, the method may further include, subsequent to block S20: sending the evaluation result to the terminal so that the terminal can display the received evaluation result.

In this embodiment, by sending the evaluation result to the terminal and displaying the received evaluation result on the terminal, the user can view the evaluation result in a timely fashion.

According to the method for evaluating cooking quality provided by this embodiment, an assessment result corresponding to a food is retrieved in response to receiving evaluation information of the food sent by a terminal. Then an evaluation result of the cooking quality of the cooking appliance is determined based on the assessment result, the evaluation information, and a preset evaluation rule. Thus, both the assessment result and the evaluation information are weighted in computing the evaluation result of the cooking quality of the cooking appliance. Such an evaluation result not only reflects the users' subjective evaluation of the cooking quality, but it also reflects an objective and tenable evaluation of the cooking quality, making the evaluation of the cooking quality of the cooking appliance more reasonable.

Figure 2:
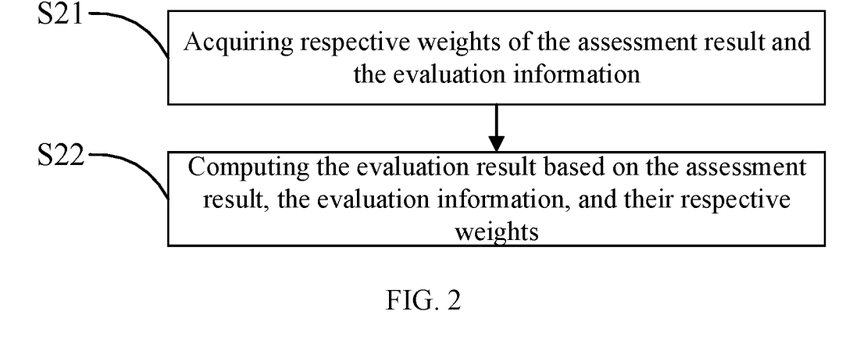
FIG. 2 is a detailed flowchart illustrating determination of an evaluation result of the cooking quality of a cooking appliance in a second embodiment of the method for evaluating cooking quality in accordance with the disclosure.

Further provided on the basis of the first embodiment is a second embodiment of the method for evaluating cooking quality, as illustrated in FIG. 2 in accordance with the disclosure. In this embodiment, the cooking appliance is a rice cooker, and block S20 may comprise the following blocks S21 and S22.

In block S21, the respective weights of the assessment result and the evaluation information are acquired.

In block S22, the evaluation result is computed based on the assessment result, the evaluation information, and their respective weights.

In this embodiment, weights may be configured for the assessment result and the evaluation information, respectively, and each weight may be configured in a reasonable manner. The server may then compute the evaluation result based on the assessment result, the evaluation information as well as their respective weights. More particularly, the evaluation result may be an addition of a product of the assessment result and its corresponding weight and a product of the evaluation information and its corresponding weight.

Further, in one embodiment the food is rice, and block S21 may include: acquiring a type of the rice; and acquiring the respective weights of the assessment result and the evaluation information according to the rice type.

In this embodiment, different varieties of rice may correspond to different weights, so by acquiring the type of the rice and then acquiring the respective weights of the assessment result and the evaluation information according to the rice type, the evaluation result can be computed based on the weights of different rice varieties.

According to the method for evaluating cooking quality provided by this embodiment, the respective weights of the assessment result and the evaluation information are acquired, and then the evaluation result is computed based on the assessment result, the evaluation information as well as their respective weights. Thus, by computing the evaluation result using the assessment result, the evaluation information, and their respective weights, the evaluation result of the cooking quality of the cooking appliance can be made more reasonable.

Figure 3:
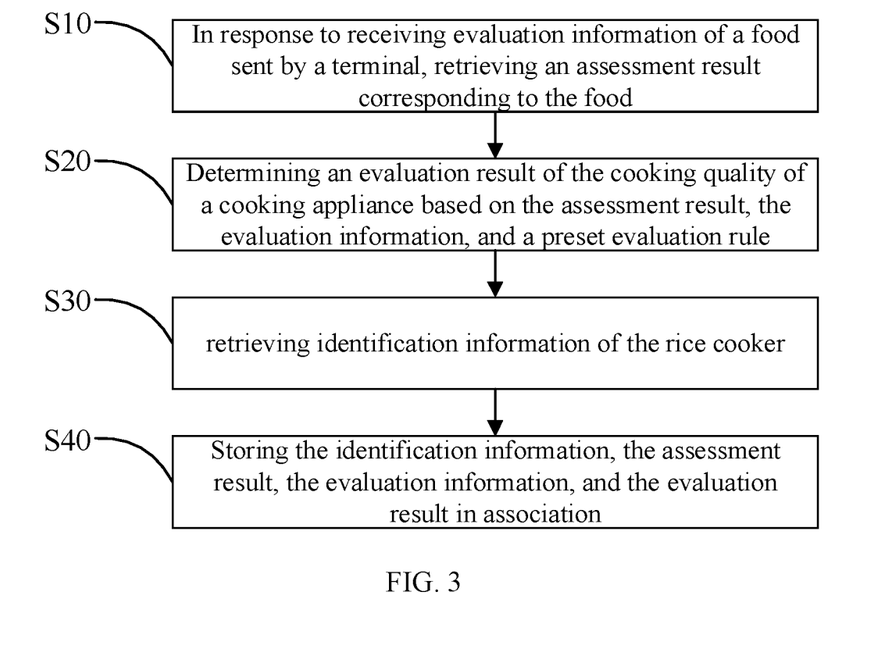
FIG. 3 is an illustrative flowchart of a third embodiment of the method for evaluating cooking quality in accordance with the disclosure.

Still further provided on the basis of the first embodiment is a third embodiment of the method for evaluating cooking quality, as illustrated in FIG. 3 in accordance with the disclosure. In this embodiment, the cooking appliance is a rice cooker, and the method may further include the following blocks S30 and S40 subsequent to block S20.

In block S30, the identification information of the rice cooker is retrieved.

The identification information of the rice cooker may be a corresponding serial number of the rice cooker.

In block S40, the identification information, the assessment result, the evaluation information, and the evaluation result are stored in association.

In this embodiment, after retrieving the identification information of the rice cooker, the server may store the identification information, the assessment result, the evaluation information, and the evaluation result in association to facilitate subsequent analysis of the stored data. For example, when the amount of data corresponding to the same identification information reaches a first preset value, the data corresponding to the same identification information may be analyzed to determine an assessment result when the evaluation information is greater than a threshold value—i.e., when the user evaluation is relatively good—and then the cooking control information corresponding to this assessment result can be acquired for subsequently controlling the rice cooker to perform cooking control in accordance with the acquired cooking control information. When the total amount of data reaches a second preset value, the position of the rice cooker corresponding to each piece of identification information may be acquired, and then the identification information, the assessment results, the evaluation information, and the evaluation results of the rice cookers with the same position information can be obtained; alternatively, a location may be selected, and then the identification information, the assessment results, the evaluation information, as well as the evaluation results of the rice cookers with a distance from this location less than a preset distance can be obtained, and further the obtained data can be analyzed to determine the region's diet or characteristics and so on.

According to the method for evaluating cooking quality provided by this embodiment, the identification information of the rice cooker is retrieved and then the identification information, the assessment result, the evaluation information as well as the evaluation result are stored in association. Therefore, by storing the above information in association, the subsequent data analysis and processing can be facilitated.

Figure 4:
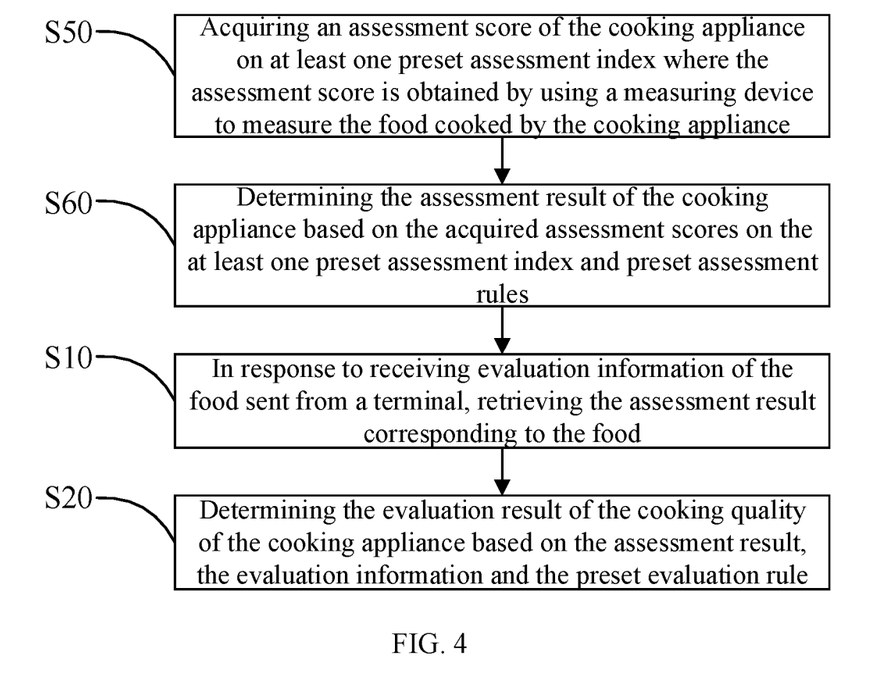
FIG. 4 is an illustrative flowchart of a fourth embodiment of the method for evaluating cooking quality in accordance with the disclosure.

Still further provided based on the first embodiment is a fourth embodiment of the method for evaluating cooking quality, as illustrated in FIG. 4 in accordance with the disclosure. In this embodiment, the method may further comprise the following blocks S50 and S60 prior to block S10.

In block S50, an assessment score of the cooking appliance on each preset assessment index is retrieved, where the assessment score is obtained by using a measuring device to measure the food cooked by the cooking appliance.

In block S60, the assessment result of the cooking quality of the cooking appliance is determined based on the acquired assessment score on each preset assessment index and a preset assessment rule.

In one embodiment, block S50 may specifically include: acquiring a measurement value obtained by measuring the food cooked by the cooking appliance using a measuring device corresponding to the preset assessment index; and determining a corresponding assessment score of the cooking appliance on the preset assessment index based on the acquired measurement value.

For each preset assessment index, there may be a corresponding measuring device to measure the cooked rice. It will be appreciated that in order to obtain measurement values with relatively high accuracy, the measurement should be performed as soon as possible after the cooking of the rice is completed, avoiding an excessive time lag.

In this embodiment, the preset assessment indexes may include one or more of the following dimensions: surface flatness, loftiness, expansion rate, water content, hardness, and gelatinization degree. Typically, in order to improve the accuracy and practicability of the assessment scores, the preset assessment indexes may not be limited to the above parameters, and different parameters may be configured for different kinds of food. For example, different parameters may be configured for different varieties of rice so that assessment scores with different emphases can be obtained for different rice varieties. Of course, different parameters may also be adopted with the same type of rice—for example, different parameters may be configured for different user groups.

Figure 5:
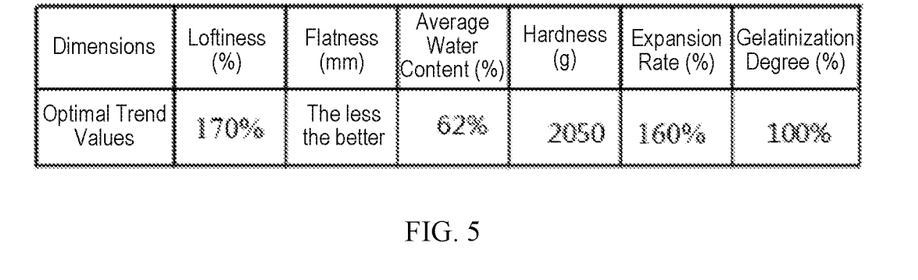
FIG. 5 illustrates optimal trend values of various preset assessment indexes in a fourth embodiment of the method for evaluating the cooking quality of a cooking appliance in accordance with the disclosure.

Optionally, the following description is made with each of the above dimensions included as an example. These dimensions can reflect relevant qualities of the food in terms of appearance, uniformity, palatability and taste. As illustrated in FIG. 5, there is given the optimal trend value of each preset assessment index.

In measurement of the surface flatness, the surface flatness of the rice generally refers to the difference between the highest point and the lowest point of the rice surface. An instrument that measures the rice surface flatness can be used to measure the rice. For example, the instrument can measure multiple points, and an average value of the measurement values of the multiple measured points can be taken as the final measurement value. The smaller the value of the surface flatness measured, the better the surface flatness of the rice.

For the measurement of loftiness and expansion rate, there is a specialized measuring device for measuring the loftiness of rice. The loftiness and expansion rate of the rice are typically expressed as percentages. The higher the loftiness and expansion rate, the better the cooking performance of the cooking appliance. Surface flatness, loftiness, and expansion rate represent the appearance of rice. Therefore, the cooking quality of the cooking appliance in terms of food appearance can be measured by measurement of these indexes.

For the measurement of water content, hardness, and gelatinization degree, the appropriate measuring instruments can be used for measuring to obtain the corresponding measurement values. Different values of the water content, hardness, and gelatinization degree may reflect different palatability.

A corresponding scoring method can be configured for the assessment index, and after obtaining the measurement value on the above assessment index, the assessment score may be obtained according to the scoring method.

In particular, as an implementation, the operation of determining a corresponding assessment score of the cooking appliance on a preset assessment index based on the acquired measurement value may include: determining a measurement value interval to which the measurement value belongs; and taking a corresponding assessment score of the measurement value interval as the corresponding assessment score of the food on the preset assessment index.

In another embodiment there may be multiple preset assessment indexes, and block S20 may specifically include: acquiring a corresponding weight of each preset assessment index; and computing the assessment result of the cooking appliance based on the assessment score of each preset assessment index and its corresponding weight.

The weight of each preset assessment index may be set in advance as appropriate, and the weights of all the preset assessment indexes should add up to 1.

Figure 6:
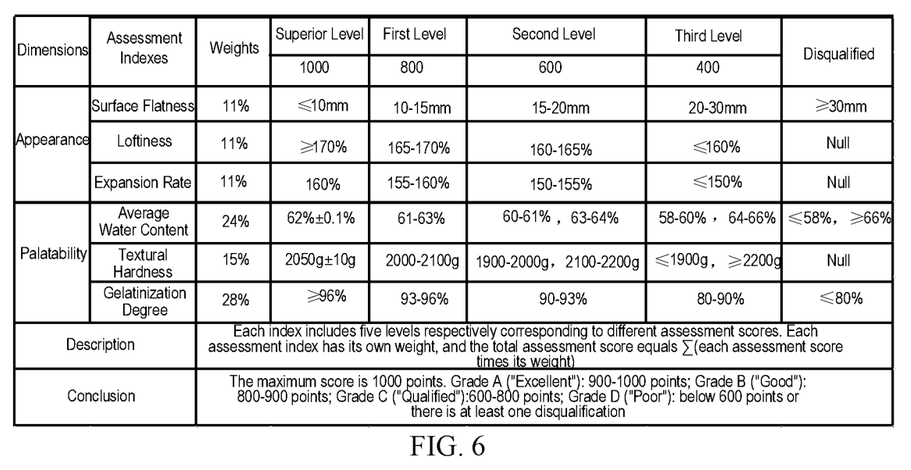
FIG. 6 illustrates a method for scoring on each preset assessment index in the fourth embodiment of the method for evaluating the cooking quality of a cooking appliance in accordance with the disclosure.

Referring now to FIG. 6 which is a schematic diagram illustrating a corresponding weight of each preset assessment index and a level division under each preset assessment index according to an embodiment. The measurement values can be divided into a plurality of intervals with each measurement value interval corresponding to an assessment score. After a measurement value is obtained, the measurement value can be input to the assessment system, which would then search for the corresponding measurement value interval and then retrieve and output the corresponding assessment score of this measurement value interval as the assessment score of the corresponding assessment index. With regards to the surface flatness, for example, the surface flatness may be divided into five measurement value intervals: "less than or equal to 10 mm" "10 to 15 mm", "15 to 20 mm" "20 to 30 m" and "more than or equal to 30 mm". Each assessment index may use a permillage system with a maximum score of 1000 points. The interval of less than or equal to 10 mm may correspond to a score of 1000 points, the interval of 10 to 15 mm may correspond to a score of 800 points, the interval of 15 to 20 mm may correspond to a score of 600 points, the interval of 20 to 30 mm may correspond to a score of 400 points, and the interval of more than or equal to 30 mm may correspond to a score of 0 points. The cooking quality of the cooking appliance model P-1 is measured. Three cooking appliances of model P-1 are used to cook rice and the respective flatness of the rice cooked thereof are 8 mm, 10 mm, and 12 mm. So an average value of these three numbers is 10 mm, which corresponds to an assessment score of 1000 points. In this fashion, the assessment score under each preset assessment index can be obtained, and further these assessment scores can be combined with their respective weights to calculate the total assessment score of the cooking appliance of this model as the assessment result of this model. Optionally, levels may be set under each assessment index. For example, 1000 points may correspond to a superior level, 800 points may correspond to the first level, 600 points may correspond to the second level, 400 points may correspond to the third level, and less than 400 points may indicate disqualification. Assessment levels may be configured for different total assessment scores. For example, if the total score is 1000 points, then the corresponding level is Grade A: Excellent; if the total score lies in the range of 900 to 1000 points, then the corresponding level is Grade B: Good; if the total score lies in the range of 800-900 points, then the corresponding level is Grade C: Qualified; if the total score lies below 600 points or there is at least one disqualification, then the corresponding level is Grade D: Poor.

It will be appreciated that the above-mentioned score system and the corresponding grades can be set as required by the user—for example, in other embodiments, the above-described score system can also be set as a percentage system, or more grades can be divided. Furthermore, in other embodiments, the measurement values can be converted to assessment scores based on preset linear relationships between the measurement values and the assessment scores.

It will be appreciated that the method according to this embodiment can be used to assess cooking appliances of multiple different models and brands. In addition, to ensure the fairness of the assessment, the same food or ingredient would be used for the assessment. In obtaining the assessment score on each assessment index for the same model of cooking appliances, multiple cooking appliances of the same model may be assessed and the assessment scores of the multiple cooking appliances may then be averaged and taken as the final assessment score of the cooking appliance of this model. In this fashion, the assessment score on each assessment index can be obtained and so the final assessment result of the cooking appliance of this model can be obtained.

According to the method for evaluating cooking quality in accordance with this embodiment, measuring devices are used to measure the food cooked by the cooking appliance to obtain the assessment scores of the cooking appliance on the preset assessment indexes, an then the assessment result of the cooking quality of the cooking appliance can then be determined based on the obtained assessment scores on the preset assessment indexes as well as the preset assessment rules. Therefore, measuring devices are used to measure the preset assessment indexes to obtain the assessment result, which is on objective and tenable score rather than a subjective assessment score based on tasters' tasting the food. Therefore, the evaluation result can not only reflect the users' subjective evaluation of the cooking quality, but it can also reflect an objective and tenable evaluation of the cooking quality, making the evaluation result of the cooking quality of the cooking appliance more reasonable.

A device for evaluating cooking quality is also provided.

Figure 7:
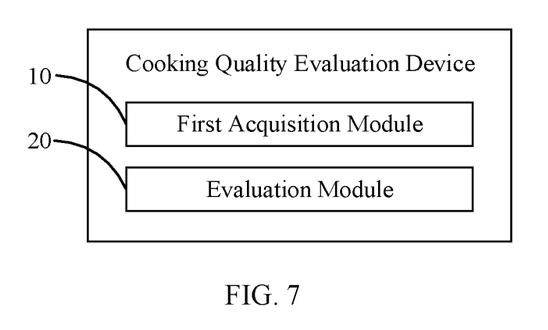
FIG. 7 is an illustrative block diagram of a first embodiment of a device for evaluating cooking quality in accordance with the disclosure.

Referring now to FIG. 7 which is an illustrative block diagram of a first embodiment of a device for evaluating cooking quality (hereinafter interchangeably referred to as cooking quality evaluating device) in accordance with the disclosure.

In this embodiment, the cooking quality evaluation device may include a first acquisition module 10 and an evaluation module 20.

The first acquisition module 10 is configured for retrieving an assessment result corresponding to a food in response to receiving evaluation information of the food sent by a terminal, the assessment result being an assessment result of the cooking quality of a cooking appliance.

In this embodiment, in response to receiving evaluation information of a food sent by a terminal, the first acquisition module 10 may retrieve the assessment result of the cooking quality of the cooking appliance corresponding to the food. In particular, the first acquisition module 10 may first retrieve the identification information of the cooking appliance corresponding to the food, and then retrieve the assessment result of the cooking quality of the cooking appliance corresponding to the identification information from among the stored cooking quality assessment results; alternatively, the first acquisition module 10 may send an assessment result retrieval instruction containing this identification information to the device used for evaluating the cooking quality of a cooking appliance, so that the evaluation device that is used for evaluating the cooking quality of a cooking appliance can return the cooking quality assessment result of the cooking appliance corresponding to the identification information.

It should be noted that users may score on a terminal such as a mobile phone on the aroma, color, taste, shape, hardness, etc., of the rice. For example, the user may input scores or grades on the terminal with regards to the aroma, color, taste, shape, hardness, etc. of the rice, and the terminal may then generate evaluation information based on the scores or grades input by the users, where the evaluation information may be an evaluation score or an evaluation grade. Users can also make an overall evaluation of the rice; that is, a user may enter only one evaluation score or evaluation grade.

The evaluation module 20 is configured for determining an evaluation result of the cooking quality of the cooking appliance based on the assessment result, the evaluation information, and a preset evaluation rule.

In some embodiments, the assessment result is an assessment score of the cooking quality of the cooking appliance. The evaluation information is an evaluation grade which can be converted to an evaluation score according to the grade ranking rules. For example, the evaluation grades may include three levels "excellent," "good," and "poor". In the case where the maximum score is 100 points, for example, "excellent" would represent a score of 85 points and above, "good" would represent a score between 60 to 84 points, and "poor" would represent a score below 60 points. If the received evaluation grade is "excellent", then this evaluation grade can be converted to an evaluation score of 90 points or it can also be converted to a score of 95 points.

In this embodiment, the evaluation module 20 may determine the evaluation result of the cooking quality of the cooking appliance based on the assessment result, the evaluation information, and the preset evaluation rule. In particular, the preset evaluation rule may include respective weights of the assessment result and the evaluation information so that the evaluation module 20 can compute the evaluation result based on the assessment result, the evaluation information, and their respective weights.

Further in one embodiment, the cooking quality evaluation device may further include a transmission module configured for sending the evaluation result to the terminal so that the terminal can display the received evaluation result.

In this embodiment, by sending via the transmission module the evaluation result to the terminal and displaying the received evaluation result on the terminal, the user can view the evaluation result in a timely fashion.

According to the device for evaluating cooking quality provided by this embodiment, the first acquisition module 10 retrieves an assessment result corresponding to a food in response to receiving evaluation information of the food sent by a terminal. Then the evaluation module 20 determines an evaluation result of the cooking quality of the cooking appliance based on the assessment result, the evaluation information, and a preset evaluation rule. Thus, both the assessment result and the evaluation information are weighted in obtaining obtain the evaluation result of the cooking quality of the cooking appliance. Such an evaluation result not only reflects the users' subjective evaluation of the cooking quality, but it also reflects an objective and tenable evaluation of the cooking quality, making the evaluation of the cooking quality of the cooking appliance more reasonable.

Figure 8:
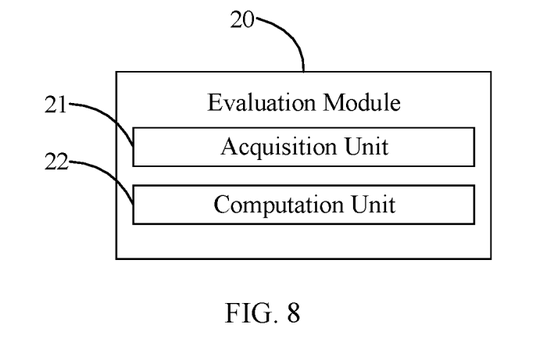
FIG. 8 is a detailed block diagram of an evaluation module in a second embodiment of the device for evaluating cooking quality in accordance with the disclosure.

Further provided on the basis of the first device embodiment is a second embodiment of the device for evaluating cooking quality, as illustrated in FIG. 8 in accordance with the disclosure. In this embodiment, the cooking appliance is a rice cooker, and the evaluation module 20 may include an acquisition unit 21 configured for acquiring respective weights of the assessment result and the evaluation information and a computation unit 22 configured for computing the evaluation result based on the assessment result, the evaluation information, and their respective weights.

Further, in one embodiment the food is rice, and the acquisition unit 21 may include a first acquisition subunit configured for acquiring a type of the rice and a second acquisition subunit configured for acquiring the respective weights of the assessment result and the evaluation information based on the rice type.

In this embodiment, different varieties of rice may correspond to different weights, so by acquiring the type of the rice and then acquiring the respective weights of the assessment result and the evaluation information according to the rice type, the evaluation result can be computed based on the weights of different rice varieties.

In this embodiment, weights can be configured for the assessment result and the evaluation information, respectively, and each weight may be configured in a reasonable manner. The computation unit 22 may then calculate the evaluation result based on the assessment result, the evaluation information as well as their respective weights. In particular, the evaluation result may be an addition of a product of the assessment result and its corresponding weight and a product of the evaluation information and its corresponding weight.

According to the device for evaluating cooking quality provided by this embodiment, the acquisition unit 21 may acquire the respective weights of the assessment result and the evaluation information, and then the computation unit 22 can calculate the evaluation result based on the assessment result, the evaluation information as well as their respective weights. Thus, by computing the evaluation result based on the assessment result, the evaluation information, and their respective weights, the evaluation result of the cooking quality of the cooking appliance can be made more reasonable.

Figure 9:
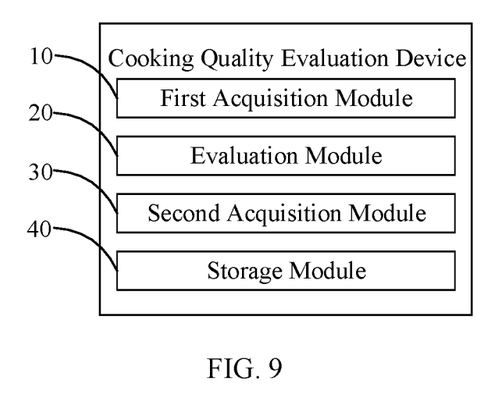
FIG. 9 is an illustrative block diagram of a third embodiment of the device for evaluating cooking quality in accordance with the disclosure.

Still further provided on the basis of the first device embodiment is a third embodiment of the device for evaluating cooking quality, as illustrated in FIG. 9 in accordance with the disclosure. In this embodiment, the cooking appliance is a rice cooker, and the cooking quality evaluation device may further include a second acquisition module 30 and a storage module 40.

The second acquisition module 30 can be configured for retrieving identification information of the rice cooker.

The identification information of the rice cooker may be a corresponding serial number of the rice cooker.

The storage module 40 can be configured for storing the identification information, the assessment result, the evaluation information, and the evaluation result in association.

In this embodiment, after retrieving the identification information of the rice cooker, the server can store the identification information, the assessment result, the evaluation information, and the evaluation result in association to facilitate subsequent analysis of the stored data. For example, when the amount of data corresponding to the same identification information reaches a first preset value, the data corresponding to the same identification information can be analyzed to determine an assessment result when the evaluation information is greater than a threshold value—i.e., when the user evaluation is relatively good— and then the cooking control information corresponding to this assessment result can be acquired for subsequently controlling the rice cooker to perform cooking control in accordance with the acquired cooking control information. When the total amount of data reaches a second preset value, the position of the rice cooker corresponding to each piece of identification information may be acquired, and then the identification information, the assessment results, the evaluation information, and the evaluation results of the rice cookers with the same position information can be obtained; alternatively, a location may be selected, and then the identification information, the assessment results, the evaluation information, as well as the evaluation results of the rice cookers with a distance from this location less than a preset distance can be obtained, and further the obtained data can be analyzed to determine the region's diet or characteristics and so on.

According to the device for evaluating cooking quality provided by this embodiment, the second acquisition module 30 can retrieve the identification information of the rice cooker, and then the storage module 40 can the identification information, the assessment result, the evaluation information as well as the evaluation result in association. Therefore, by storing the above information in association, the subsequent data analysis and processing can be facilitated.

Figure 10:
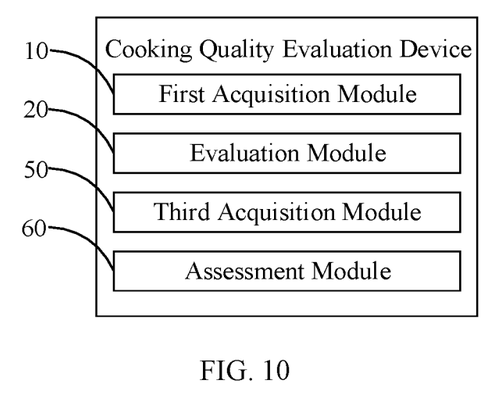
FIG. 10 is an illustrative block diagram of a fourth embodiment of the device for evaluating cooking quality in accordance with the disclosure.

Still further provided based on the first device embodiment is a fourth embodiment of the device for evaluating cooking quality, as illustrated in FIG. 10 in accordance with this disclosure. In this embodiment the cooking quality evaluation device may further include: a third acquisition module 50 configured for acquiring an assessment score of the cooking appliance on a preset assessment index where the assessment score is obtained by using a measuring device to measure the food cooked by the cooking appliance; and an assessment module 60 configured for determining the assessment result of the cooking quality of the cooking appliance based on the acquired assessment score on the preset assessment index and preset assessment rules.

In one embodiment, the third acquisition module 50 may specifically include: a measurement acquisition unit configured for acquiring a measurement value obtained by using a measuring device corresponding to a preset assessment index to measure the food cooked by the cooking appliance and a score determination unit configured for determining a corresponding assessment score of the cooking appliance on the preset assessment index based on the acquired measurement value.

For each preset assessment index, there may be a corresponding measuring device to measure the cooked rice. It will be appreciated that in order to obtain measurement values with relatively high accuracy, the measurement should be performed as soon as possible after the cooking of the rice is completed, avoiding an excessive time lag.

In this embodiment, the preset assessment indexes may include one or more of the following dimensions: surface flatness, loftiness, expansion rate, water content, hardness, and gelatinization degree. Typically, in order to improve the accuracy and practicability of the assessment scores, the preset assessment indexes may not be limited to the above parameters, and different parameters may be configured for different kinds of food. For example, different parameters may be configured for different varieties of rice so that assessment scores with different emphases can be obtained for different rice varieties. Of course, different parameters may also be adopted with the same type of rice—for example, different parameters may be configured for different user groups.

Optionally, the following description is made with each of the above nine dimensions included as an example. These nine dimensions can reflect relevant qualities of the food in terms of appearance, uniformity, palatability and taste. As illustrated in FIG. 5, there is given the optimal trend value of each preset assessment index.

In measurement of the surface flatness, the surface flatness of the rice generally refers to the difference between the highest point and the lowest point of the rice surface. An instrument that measures the rice surface flatness can be used to measure the rice. For example, the instrument can measure multiple points, and an average value of the measurement values of the multiple measured points can be taken as the final measurement value. The smaller the value of the surface flatness measured, the better the surface flatness of the rice.

For the measurement of loftiness and expansion rate, there is a specialized measuring device for measuring the loftiness of rice. The loftiness and expansion rate of the rice are typically expressed as percentages. The higher the loftiness and expansion rate, the better the cooking performance of the cooking appliance. Surface flatness, loftiness, and expansion rate represent the appearance of rice. Therefore, the cooking quality of the cooking appliance in terms of food appearance can be measured by measurement of these indexes.

For the measurement of water content, hardness, and gelatinization degree, the appropriate measuring instruments can be used for measuring to obtain the corresponding measurement values. Different values of the water content, hardness, and gelatinization degree may reflect different palatability.

A corresponding scoring device can be configured for the assessment index, and after the measurement acquisition unit acquires the measurement value on the above assessment index, the score determination unit can obtain the assessment score according to the scoring method.

In particular, as an implementation, the score determination unit may further be configured for: determining a measurement value interval to which the measurement value belongs; and taking a corresponding assessment score of the measurement value interval as the corresponding assessment score of the food on the preset assessment index.

Typically, in another embodiment there may be multiple preset assessment indexes, and the assessment module 60 may include: a weight acquisition module configured for acquiring a corresponding weight of each preset assessment score; and a result computation module configured for computing the assessment result of the cooking appliance based on the assessment score of each preset assessment index and its corresponding weight.

The weight of each preset assessment index may be set in advance as appropriated, and the weights of all the preset assessment indexes should add up to 1.

Referring back to FIG. 6 which is a schematic diagram illustrating a corresponding weight of each preset assessment index and a level division under each preset assessment index according to an embodiment. The measurement values can be divided into a plurality of intervals with each measurement value interval corresponding to an assessment score. After a measurement value is obtained, the measurement value can be input to the assessment system, and then the assessment system would search for the corresponding measurement value interval and then retrieve and output the corresponding assessment score of this measurement value interval as the assessment score of the corresponding assessment index. With regards to the surface flatness, for example, the surface flatness may be divided into five measurement value intervals: "less than or equal to 10 mm" "10 to 15 mm", "15 to 20 mm" "20 to 30 m" and "more than or equal to 30 mm". Each assessment index may use a permillage system with a maximum score of 1000 points. The interval of less than or equal to 10 mm may correspond to a score of 1000 points, the interval of 10 to 15 mm may correspond to a score of 800 points, the interval of 15 to 20 mm may correspond to a score of 600 points, the interval of 20 to 30 mm may correspond to a score of 400 points, and the interval of more than or equal to 30 mm may correspond to a score of 0 points. The cooking quality of the cooking appliance model P-1 is measured. Three cooking appliances of model P-1 are used to cook rice and the respective flatness of the rice cooked thereof are 8 mm, 10 mm, and 12 mm. So an average value of these three numbers is 10 mm, which corresponds to an assessment score of 1000 points. In this fashion, the assessment module 60 can obtain the assessment score under each preset assessment index, and further combine these assessments scores with their respective weights to calculate the total assessment score of the cooking appliance of this model as the assessment result of this model. Optionally, levels may be set under each assessment index. For example, 1000 points may correspond to a superior level, 800 points may correspond to the first level, 600 points may correspond to the second level, 400 points may correspond to the third level, and less than 400 points may indicate disqualification. Assessment levels may be configured for different total assessment scores. For example, if the total score is 1000 points, then the corresponding level is Grade A: Excellent; if the total score lies in the range of 900 to 1000 points, then the corresponding level is Grade B: Good; if the total score lies in the range of 800-900 points, then the corresponding level is Grade C: Qualified; if the total score lies below 600 points or there is at least one disqualification, then the corresponding level would be Grade D: Poor.

It will be appreciated that the above-mentioned score system and the corresponding grades can be set as required by the user—for example, in other embodiments, the above-described score system can also be set as a percentage system, or more grades can be divided. Furthermore, in other embodiments, the measurement values can be converted to assessment scores based on preset linear relationships between the measurement values and the assessment scores.

It will be appreciated that the device according to this embodiment can be used to assess cooking appliances of multiple different models and brands. In addition, to ensure the fairness of the assessment, the same food or ingredient would be used for the assessment. In obtaining the assessment score on each assessment index for the same model of cooking appliances, multiple cooking appliances of the same model may be assessed and the assessment scores of the multiple cooking appliances may then be averaged and taken as the final assessment score of the cooking appliance of this model. In this fashion, the assessment score on each assessment index can be obtained and so the final assessment result of the cooking appliance of this model can be obtained.

According to the cooking quality evaluation device according to this embodiment, the third acquisition module 50 can acquire the assessment scores of the cooking appliance on the preset assessment indexes where the assessment scores are obtained by using measuring devices to measure the food cooked by the cooking appliance, and then the assessment module 60 can determine the assessment result of the cooking quality of the cooking appliance based on the obtained assessment scores on the preset assessment indexes as well as the preset assessment rules. Therefore, measuring devices are used to measure the preset assessment indexes to obtain the assessment result, which is on objective and tenable score rather than a subjective assessment score based on tasters' tasting the food. Therefore, the evaluation result can not only reflect the users' subjective evaluation of the cooking quality, but it can also reflect an objective and tenable evaluation of the cooking quality, making the evaluation result of the cooking quality of the cooking appliance more reasonable.

Furthermore, it will be apparent to those skilled in the art that this disclosure also provides a cooking quality evaluation device that comprises a non-transitory program storage medium and one or more processors. The non-transitory program storage medium stores program code executable by the one or more processors to perform the various methods, processes, or flows described supra. In addition, it will be apparent to those skilled in the art that various modules or units or subunits 10, 20, 21, 22, 30, 40, 50, and 60 as illustrated in FIGS. 7 through 10 can be software modules or software units or subunits. In another aspect, it is well-known that various software modules or units or subunits inherently can be stored in the non-transitory program storage medium and executed by the one or more processors.

The foregoing merely depicts some exemplary embodiments of this disclosure and is not intended as limiting the patentable scope of this disclosure. Any equivalent configurational or flow transformations made taking advantage of the description and accompanying drawings of this disclosure, or any direct or indirect applications of the disclosure in other related technical fields will all be compassed within the patentable scope of this disclosure.

What is claimed is:

1. A method for evaluating cooking quality, comprising:
   receiving evaluation information of a food sent by a terminal;
   retrieving an assessment result corresponding to the food, the assessment result being an assessment result of cooking quality of a cooking appliance used to cook the food, wherein the assessment result includes a measurement of two or more of: loftiness, expansion rate, water content, hardness, and gelatinization degree of the food cooked by the cooking appliance; and
   determining an evaluation result of the cooking quality of the cooking appliance based on the assessment result, the evaluation information, and a preset evaluation rule, including:
   acquiring respective weights of the assessment result and the evaluation information, wherein the weights all the assessment results add up to 1; and
   computing the evaluation result based on the assessment result, the evaluation information, and the respective weights of the assessment result and the evaluation information.

2. The method of claim 1, wherein the food is rice, and acquiring the respective weights of the assessment result and the evaluation information comprises:
   acquiring a type of the rice; and
   acquiring the respective weights of the assessment result and the evaluation information according to the type of the rice.

3. The method of claim 1, wherein the cooking appliance is a rice cooker, and the method further comprises, subsequent to determining the evaluation result of the cooking quality of the cooking appliance:
   retrieving identification information of the rice cooker; and
   storing in association the identification information, the assessment result, the evaluation information, and the evaluation result.

4. The method of claim 1, further comprising:
   subsequent to determining the evaluation result of the cooking quality of the cooking appliance, sending the evaluation result to the terminal for display.

5. The method of claim 1, further comprising:
   prior to retrieving the assessment result of the cooking quality of the cooking appliance corresponding to the food:
   acquiring an assessment score of the cooking appliance on at least one preset assessment index, the assessment score being obtained by using a measuring device to measure the food cooked by the cooking appliance; and
   determining the assessment result of the cooking quality of the cooking appliance based on the acquired assessment score on the at least one preset assessment index and preset assessment rules.

6. The method of claim 5, wherein the cooking appliance is a rice cooker, and determining the evaluation result of the cooking quality of the cooking appliance comprises:
   acquiring respective weights of the assessment result and the evaluation information; and
   computing the evaluation result based on the assessment result, the evaluation information, and the respective weights of the assessment result and the evaluation information.

7. The method of claim 6, wherein the food is rice, and acquiring the respective weights of the assessment result and the evaluation information comprises:
   acquiring a type of the rice; and
   acquiring the respective weights of the assessment result and the evaluation information according to the type of the rice.

8. The method of claim 5, wherein the cooking appliance is a rice cooker, and the method further comprises, subsequent to determining the evaluation result of the cooking quality of the cooking appliance:
   acquiring identification information of the rice cooker; and
   storing in association the identification information, the assessment result, the evaluation information, and the evaluation result.

9. The method of claim 5, further comprising:
   subsequent to determining the evaluation result of the cooking quality of the cooking appliance, sending the evaluation result to the terminal for display.

10. A device for evaluating cooking quality, comprising one or more processors and a non-transitory program storage medium storing program code executable by the one or more processors, the program code comprising:
   a first acquisition module configured to retrieve an assessment result corresponding to a food in response to receiving evaluation information of the food sent by a terminal, the assessment result being an assessment result of the cooking quality of a cooking appliance used to cook the food, wherein the assessment result includes a measurement of two or more of: loftiness, expansion rate, water content, hardness, and gelatinization degree of the food cooked by the cooking appliance; and
   an evaluation module configured to determine an evaluation result of the cooking quality of the cooking appliance based on the assessment result, the evaluation information, and a preset evaluation rule, including:
   acquiring respective weights of the assessment result and the evaluation information, wherein the weights all the assessment results add up to 1; and computing the evaluation result based on the assessment result, the evaluation information, and the respective weights of the assessment result and the evaluation information.

11. The device of claim 10, wherein the food is rice, and the acquisition unit comprises:
    a first acquisition subunit configured to acquire a type of the rice; and
    a second acquisition subunit configured to acquire the respective weights of the assessment result and the evaluation information according to the type of the rice.

12. The device of claim 10, wherein the cooking appliance is a rice cooker, and the device further comprises:
    a second acquisition module configured to acquire identification information of the rice cooker; and
    a storage module configured to store in association the identification information, the assessment result, the evaluation information, and the evaluation result.

13. The device of claim 10, further comprising:
    a transmission module configured to send the evaluation result to the terminal for display.

14. The device of claim 10, further comprising:
    a third acquisition module configured to acquire an assessment score of the cooking appliance on at least one preset assessment index, the assessment score being obtained by using a measuring device to measure the food cooked by the cooking appliance; and
    an assessment module configured to determine the assessment result of the cooking quality of the cooking appliance based on the acquired assessment score on the at least one preset assessment index and preset assessment rules.

15. The device of claim 14, wherein the cooking appliance is a rice cooker, and the evaluation module comprises:
    an acquisition unit configured to acquire respective weights of the assessment result and the evaluation information; and
    a computation unit configured to compute the evaluation result based on the assessment result, the evaluation information, and the respective weights of the assessment result and the evaluation information.

16. The device of claim 15, wherein the food is rice, and the acquisition unit comprises:
    a first acquisition subunit configured to acquire a type of the rice; and
    a second acquisition subunit configured to acquire the respective weights of the assessment result and the evaluation information according to the type of the rice.

17. The device of claim 14, wherein the cooking appliance is a rice cooker, and the device further comprises:
    a second acquisition module configured to acquire identification information of the rice cooker; and
    a storage module configured to store in association the identification information, the assessment result, the evaluation information, and the evaluation result.

18. The device of claim 14, further comprising:
    a transmission module configured to send the evaluation result to the terminal for display.

* * * * *